United States Patent [19]

Freeman et al.

[11] Patent Number: 4,985,143
[45] Date of Patent: Jan. 15, 1991

[54] METHOD FOR PACKING CHROMATOGRAPHIC BEDS

[75] Inventors: David H. Freeman, Potomac; Rosalie M. Angeles, Germantown; Suzanne Keller, Rockville, all of Md.

[73] Assignee: The University of Maryland, College Park, Md.

[21] Appl. No.: 472,436

[22] Filed: Jan. 31, 1990

Related U.S. Application Data

[63] Continuation of Ser. No. 202,405, Jun. 6, 1988, abandoned.

[51] Int. Cl.$^5$ ............................................. B01D 15/08
[52] U.S. Cl. .................................. 210/198.2; 210/635; 210/657; 55/67; 55/386; 141/12; 141/34; 141/73; 141/80
[58] Field of Search ............ 210/635, 656, 657, 198.2; 141/12, 34, 71, 73, 80; 55/67, 386

[56] References Cited

U.S. PATENT DOCUMENTS

| | | | |
|---|---|---|---|
| 1,218,416 | 3/1917 | Krarup | 141/12 |
| 1,663,696 | 3/1928 | Fraas | 141/34 |
| 1,743,242 | 1/1930 | Schultze | 141/34 |
| 1,761,228 | 6/1930 | Peck | 141/34 |
| 2,071,504 | 2/1937 | Darling | 141/34 |
| 3,536,106 | 10/1970 | Anderson | 141/73 |
| 3,692,669 | 9/1972 | Bauman | 210/656 |
| 3,935,884 | 2/1976 | Hazelton | 141/80 |
| 4,116,948 | 9/1978 | Mittenzwei | 210/657 |
| 4,142,858 | 3/1979 | Acuff | 210/656 |
| 4,146,063 | 3/1979 | Karlsson | 141/34 |
| 4,175,037 | 11/1979 | Benny | 55/67 |
| 4,270,921 | 6/1981 | Graas | 210/656 |
| 4,416,783 | 11/1983 | Noguchi | 210/635 |
| 4,422,941 | 12/1983 | Vaughan | 210/657 |
| 4,483,374 | 11/1984 | Siemion | 210/656 |
| 4,549,584 | 10/1985 | Morin | 141/73 |
| 4,670,141 | 6/1987 | Shackelford | 55/386 |
| 4,737,292 | 4/1988 | Ritacco | 210/198.2 |

FOREIGN PATENT DOCUMENTS

| | | | |
|---|---|---|---|
| 148360 | 7/1985 | European Pat. Off. | 141/73 |
| 2200730 | 7/1972 | Fed. Rep. of Germany | 141/34 |
| 2943982 | 5/1981 | Fed. Rep. of Germany | 141/12 |
| 1214527 | 2/1986 | U.S.S.R. | 141/73 |

OTHER PUBLICATIONS

Snyder, Introduction to Modern Liquid Chromatography John Wiley & Sons, Inc., New York, 1979, pp. 206–216.

Mikes' Laboratory Handbook of Chromatographic and Allied Methods, John Wiley & Sons Inc., New York, 1979, p. 354.

*Primary Examiner*—Ernest G. Therkorn
*Attorney, Agent, or Firm*—Oblon, Spivak, McClelland, Maier & Neustadt

[57] ABSTRACT

Column chromatography beds are packed through the application of static force. A slurry of the chromatography bed material and a non-viscous liquid is filled into the column plugged at one end, and allowed to settle. The column is transferred to a centrifuge, and centrifuged for a brief period of time to achieve a predetermined packing level, at a range generally of 100–5,000 gravities. Thereafter, the plug is removed, other fixtures may be secured, and the liquid is allowed to flow out through the bed. This results in an evenly packed bed, with no channeling or preferential flow characteristics.

6 Claims, No Drawings

METHOD FOR PACKING CHROMATOGRAPHIC BEDS

BACKGROUND OF THE INVENTION

The government may have rights in this invention under Department of Energy Grant No. DE-FG05-85-ER/3308

This application is a continuation of application Ser. No. 202,405, filed on Jun. 6, 1988, now abandoned.

FIELD OF THE INVENTION

This invention pertains to an improved method for packing chromatographic beds, and the improved beds obtained thereby. More specifically, the invention comprises a method by which the bed is packed under centrifugal force, to improve packing characteristics while reducing time and cost.

BACKGROUND OF THE PRIOR ART

Column chromatography of all types continues to be a standard method of operation in the laboratory and the commercial marketplace for the separation of materials. The estimated market of $250–300 million for chromatography consumables, out of the billion dollar market for products for separation processes, by the year 1990, represents a 15–20% growth factor for this type of product. Although a wide variety of technologies continue to take advantage of the separation capabilities offered by modern column chromatography, one technology particularly driving the expansion of the column chromatography consumables market is generally referred to as biotechnology. In particular, the separation and purification of biologically produced materials resulting from genetic engineering technology is placing significant demands on the ability of the marketplace to meet the need to provide chromatography columns which are capable of high loadings, and rapid and reproducible results, at a reasonable price.

At the same time, the demands of technology are increasingly requiring higher precision and accuracy in the separation of exceedingly fine dimension, calling for chromatography beds which are capable of separating, in use, nearly identical fractions. Because of the nature of the product, and the increased requirements for safety, particularly in areas where human consumption is involved, it is absolutely essential that these separations be constant and reproducible, from batch to batch, laboratory to laboratory, and between commercial establishments.

One of the most commonly employed methods for creating a liquid chromatographic bed involves introducing the chromatographic material, which may be, e.g., a silica gel, into a column in the presence of a suspending liquid, with the outlet end of the column blocked, and thereafter applying a high pressure pump to the open end and removing the fitting at the outlet and, thereby draining a large volume of liquid through the bed, to pack it down.

This process, which may generally be referred to as dynamic packing, in which the liquid is pressurized and forced to flow through the bed, has significant disadvantages. In particular, flowing the liquid through the bed under pressure to achieves column compaction and frequently causes "channeling" or preferential flow characteristics, caused by the resistive flow of pressurized liquid through the bed. The application of high pressure packing techniques are labor intensive and too costly to be used to prepare disposable chromatographic columns. Otherwise, the materials employed therein are relatively inexpensive. In other instances, the use of high pressure pumps can cause laboratory damage and injury, particularly when end fittings on the column blow off under the application of pressure, the released fitting can fly off at high velocity.

Accordingly, it remains a clear need of the art to provide a method for bed packing of chromatography columns which is not labor intensive, produces accurate and reproducible results and does not expose the worker or the laboratory to the risk of injury or damage.

SUMMARY OF THE INVENTION

The invention of this application meets the above-identified need in the industry. Specifically, the process begins in a manner not dissimilar from the first step of the prior art, that is, a slurry of the bed material, suspended in a liquid, which is preferably non-viscous, is introduced into the column, the end of which has been packed, and will later be replaced with a fitting for the purpose of drawing off first the slurry liquid, and later, eluent, under conditions of use. Thereafter, the process of this invention departs from the prior art process. In particular, the bed material, which is denser than the liquid of the slurry, is allowed to briefly settle, and the column, without draining off the liquid, is thereafter transferred to a centrifuge, together with at least one additional column of equal mass. The columns are then subjected to static pressure, achieved by centrifugation. This results in rapid compaction of the bed, without the problems and dangers experienced in the prior art. The liquid is thereafter allowed to drain through the column, providing a very tightly packed chromatographic column, which is not characterized by channeling or other preferential flow phenomenon which would result in non-reproducible chromatographic performance. The overall process is neither labor intensive nor hazardous. The process requires minimal labor while the beds are formed by the settling and centrifugation steps.

DETAILED DESCRIPTION OF THE INVENTION

Virtually any particulate chromatographic material may be employed as the bed material or matrix for the chromatographic column in this invention. Typical examples include various bead-formed gels, such as the various gels available from Pharmacia, BioGels available from Bio-Rad and Ultrogel AcA available from LKB. However, such gels are recited as exemplary only and without limitation. Various other ion-exchange matrices, which may include materials prepared from polystyrene and cellulose and various other polymers, as well as widely varying affinity and immunoaffinity supports are known, and may be used in the invention addressed herein. Generally speaking, virtually any chromatographic material or support therefor, particle-like, and can be suspended in a non-viscous liquid, which has a lower density than the chromatographic material, is suitable for use in the claimed invention.

Initially, the bed material must be suspended in a liquid to form the slurry that is introduced to the column. Again, the only requirement of the liquid be that it be less dense than the material of the bed, to allow the material to centrifuge out, and form a distinct lower layer. Preferably, the liquid is one of low viscosity, and exemplary liquids include water, various alkanes, alcohols, and related liquids, in particular those which are neutral or even acidic at ambient temperature. For certain chromatographic columns and uses it is desired to impart to the surface of the bed material a particular characteristic, either a physical characteristic, such as voids and the like, or a chemical characteristic, such as an affinity or anti-affinity agent adhered thereto. Although the material may be so prepared prior to preparation of the slurry for use in the first step of this invention, it may alternatively be provided in conjunction with the formation of a slurry, when the surface characteristic can be imparted to the bed material through the agency of the liquid, such as etching through acid or base, alteration of ionic characteristics, binding of antibodies, antigens and other active agents.

The slurry is added to a chromatographic cylinder or column, fitted at the outlet end with a plug. As noted above, this plug is subsequently replaced with a fitting that allows liquid to flow out of the column. The bed material, denser than the liquid, is given the opportunity to settle to the bottom of the column to form a loosely packed bed, which, depending on the viscosity of the liquid support, can occur relatively quickly.

Once the material has at least partly settled, it, together with an extension least one other column, is placed in the cup of a centrifuge. It should be noted that it is important to insure that, at rest in the centrifuge, the level of the liquid remains above the top of the particle bed, although, given this limitation, it is advantageous after the packing process is complete that in order to realize top of the bed be located at least somewhat near the top of the column, the appreciable efficiency produced by the claimed process. The centrifuge is then brought up to a predetermined relative centrifugal force, which may be between about 1–500 gravities, but may range up above 1,000 gravities, to e.g., 5,000 gravities. It will be noted that 1,000 gravities forcefully compacts the bed, evenly, and avoids the formation of preferential flow channels along the cylinder wall, or irregular openings that may form in a bed that is not uniformly and completely compacted.

After compaction, the plug or stopper in the outlet end of the tube is removed, and the liquid is allowed to flow therethrough, providing a compacted chromatographic bed for use in separation chemistry. It should be noted that the flow of the liquid, at this point, does not introduce preferential flow channels and the like, in light of the high degree of packing in the bed already introduced.

As noted above, this process is not usually limited with regard to the nature of the material of the chromatographic bed, or the liquid support for the slurry, save for gross physical characteristics. Similarly, it is not specifically limited to column length or diameter. The limiting feature is the length of the centrifuge cup or receptacle and supporting structure, which of course can be modified at will. General examples of column dimensions include columns of a length of 5–15 cm although, again, no limitation to such length is necessary or implied. It should be noted further that, in general, a centrifuge apparatus is provided with a plurality of receptacles, so that 4 or 8, or even more columns can be centrifuged at one time. This results in a significant reduction in preparation time and effort on a per column basis, resulting in reduced preparation time with conventional material.

Relatively few parameters or limitations need be observed to practice the process of this invention, as claimed below. To improve evenness of compaction, the slurry should consist of uniformly sized particles and it should also be made free of air bubbles. This will generally be achieved through the settling step of the process. One must insure that the liquid level is above the level of the uncompacted bed, when placed in the centrifuge. As noted above, efficiency is when the top of the compacted bed is located at least slightly above its maximum length after the processing is complete. One parameter that may be observed to improve bed quality is to gradually increase the centrifuge speed, over time. Thus, if the actual centrifugation step involves application of a static force of 500 gravities for a period of three minutes, this level may be built up to gradually, extending the length of time of centrifuging for the necessary period to achieve the same overall compaction value. In this regard, it should be noted that it is appropriate to deliberately exceed the minimum settling time needed for bed compaction, as no ill effects are observed, and this may help insure uniform quality in the bed packing. In any event, the predetermined level of centrifugation, which is a product of the centrifugation time and applied force, can easily be determined emperically, without significantly raising the cost of the process.

Numerous modifications and variations of the present invention are possible in light of the above teachings. It is therefore to be understood that within the scope of the appended claims, the invention may be practiced otherwise than as specifically described herein.

What is new and desired to be secured by Letters Patent of the United States is:

1. A process for packing column chromatography beds, consisting essentially of:
    preparing a slurry of chromatographic bed material and a liquid comprising at least one of water, methanol, chloroform and hexane, the bed material being denser than the liquid,
    introducing said slurry into a column provided with a removable plug at one end and allowing said slurry to settle in said column such that said bed material falls to said plugged end,
    thereafter centrifuging said column under the condition that the surface of the liquid is at all points and times above the surface of the bed material, with respect to said plugged end, and continuing said centrifuging for a period of time to obtain a predetermined packing level in said bed material in the substantial absence of channeling,
    removing said plug from said column and allowing said liquid to drain through the bed and out of the column.

2. The process of claim 1, wherein said centrifuging is conducted at levels which generate a force at least as great as 100 gravities.

3. The method of claim 2, wherein said level of force achieved through centrifugation is 100–2,000 gravities.

4. The process of claim 1, wherein said bed material is comprised of material selected from the group consisting of silica gel, alumina powder or mixtures thereof.

5. The process of claim 1, wherein a plurality of columns are simultaneously treated.

6. The process of claim 1, wherein said bed material is comprised of a semi-rigid gel.

* * * * *